United States Patent [19]
Davies et al.

[11] Patent Number: 5,447,937
[45] Date of Patent: Sep. 5, 1995

[54] CNS ACTIVE TETRAHYDROBENZOTHIENOPYRIDINES

[75] Inventors: David T. Davies; Ian T. Forbes; Mervyn Thompson, all of Harlow, England

[73] Assignee: SmithKline Beecham p.l.c., Brentford, England

[21] Appl. No.: 196,176

[22] PCT Filed: Aug. 11, 1992

[86] PCT No.: PCT/GB92/01487
§ 371 Date: Feb. 10, 1994
§ 102(e) Date: Feb. 10, 1994

[87] PCT Pub. No.: WO93/04068
PCT Pub. Date: Mar. 4, 1993

[30] Foreign Application Priority Data
Aug. 13, 1991 [GB] United Kingdom .............. 9117459

[51] Int. Cl.$^6$ .................. A61K 31/44; C07D 495/04
[52] U.S. Cl. .................. 514/291; 514/232.8; 514/254; 544/126; 544/361; 546/80
[58] Field of Search .............. 546/80; 514/291, 232.8, 514/254; 544/126, 361

[56] References Cited
U.S. PATENT DOCUMENTS

| | | | |
|---|---|---|---|
| 3,767,659 | 10/1973 | Suh | 546/80 |
| 5,093,493 | 3/1992 | Thompson | 546/80 |
| 5,126,448 | 6/1992 | Ueki | 546/80 |

FOREIGN PATENT DOCUMENTS

| | | |
|---|---|---|
| 249301 | 12/1987 | European Pat. Off. . |
| 327223 | 8/1989 | European Pat. Off. . |
| 9117165 | 11/1991 | WIPO . |

*Primary Examiner*—Ceila Chang
*Attorney, Agent, or Firm*—Linda E. Hall; Stuart R. Suter; Edward T. Lentz

[57] ABSTRACT

Tetrahydrobenzothienopyridines of formula (I),

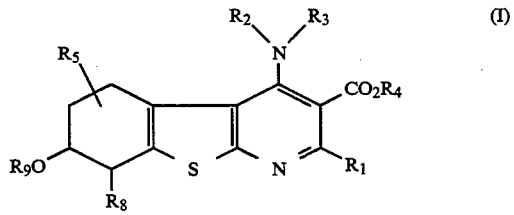

wherein, $R_1$, $R_2$, $R_3$ $R_4$, $R_5$, $R_8$ and $R_9$ are as defined in the specification and pharmaceutical compositions containing such compounds are of use in treating anxiety, convulsion and sleep disorders.

9 Claims, No Drawings

CNS ACTIVE TETRAHYDROBENZOTHIENOPYRIDINES

This application is a 371 of PCT/GB92/01487 filed Aug. 11, 1992.

This invention relates to compounds having pharmacological activity, to a process for their preparation, to compositions containing them and to their use in the treatment of mammals.

EP-A-0327223 and WO91/17165 (filed 1st May 1991) disclose certain tetrahydrobenzothienopyridines which have CNS activity, in particular anxiolytic and/or anti-depressant activity.

A class of compounds has now been discovered, which compounds have been found to have CNS activity, in particular anxiolytic and/or anti-depressant and/or anticonvulsant activity and/or possess activity useful in the treatment of sleep disorders.

Accordingly, the present invention provides a compound of formula (I) or a pharmaceutically acceptable salt thereof.

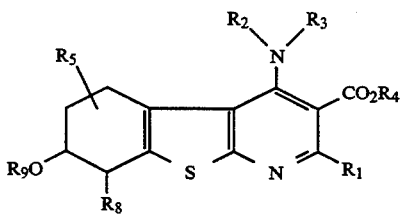

wherein:

$R_1$ is hydrogen, $C_{1-6}$ alkyl, phenyl or phenyl $C_{1-4}$ alkyl wherein the phenyl moiety is optionally substituted by one or more $C_{1-6}$ alkyl, $C_{1-6}$ alkoxy, $C_{1-6}$ alkylthio, hydroxy, $C_{2-7}$ alkanoyl, halo, trifluoromethyl, nitro, amino optionally substituted by one or two $C_{1-6}$ alkyl groups or by $C_{2-7}$ alkanoyl, cyano, carbamoyl or carboxy groups;

$R_2$ and $R_3$ are independently selected from hydrogen, $C_{1-6}$ alkyl, $C_{3-7}$ cycloalkyl, $C_{3-7}$ cycloalkyl-$C_{1-4}$ alkyl, $C_{3-6}$ alkenyl, $C_{1-7}$ alkanoyl, $C_{1-6}$ alkylsulphonyl, di-($C_{1-6}$ alkyl)amino $C_{1-6}$ alkyl, 3-oxobutyl, 3-hydroxybutyl, phenyl, phenyl $C_{1-4}$ alkyl, benzoyl, phenyl $C_{2-7}$ alkanoyl or benzenesulphonyl any of which phenyl moieties are optionally substituted by one or two halogen, $C_{1-6}$ alkyl, $C_{1-6}$ alkoxy, $CF_3$, amino or carboxy, or $R_2$ and $R_3$ together are $C_{2-6}$ polymethylene optionally interrupted by oxygen or $NR_6$ wherein $R_6$ is hydrogen or $C_{1-6}$ alkyl optionally substituted by hydroxy;

$R_5$ is hydrogen or $C_{1-6}$ alkyl and $R_8$ is hydrogen or $R_5$ and $R_8$ together form a $C_{1-6}$ alkylidene group at the 8-position;

$R_9$ is hydrogen or $C_{1-6}$ alkyl; and —$CO_2R_4$ is a pharmaceutically acceptable ester group.

Alkyl moieties within the variables $R_1$, $R_2$, $R_3$, $R_5$, $R_6$ and $R_9$ are preferably $C_{1-3}$ alkyl, such as methyl, ethyl and n- and iso-propyl.

Values for $R_1$ include hydrogen, methyl, ethyl, n- and iso-propyl, phenyl and benzyl. Preferably, $R_1$ is methyl.

It will be appreciated in selecting variables $R_2$ and $R_3$ that the nitrogen atom is not directly attached to unsaturated aliphatic carbon.

Values for $R_2$ and $R_3$ include hydrogen, methyl, ethyl, n- and iso-propyl, n-, sec-, iso- and tert-butyl, n-, sec, iso- and neo-pentyl, cyclopentyl, cyclohexyl, cycloheptyl, cyclopentyl-$C_{1-4}$ alkyl, cyclohexyl-$C_{1-4}$ alkyl and cycloheptyl-$C_{1-4}$ alkyl, where values for $C_{1-4}$ alkyl include methylene and ethylene, but-2-enyl, but-3-enyl, 1-methylprop-2-enyl, formyl, acetyl, propionyl, methylsulphonyl, 3-dimethylaminobutyl, 3-oxobutyl, 3-hydroxybutyl, phenyl, benzyl, benzoyl, benzylcarbonyl and benzenesulphonyl, or $R_2$ and $R_3$ together form —($CH_2$)$_r$—X—($CH_2$)$_s$-wherein r and s are independently 1, 2 or 3 and X is a bond, O or $NR_6$, for example $C_4$ or $C_5$ polymethylene, —($CH_2$)$_2$—O—($CH_2$)$_2$— or —($CH_2$)$_2$-$NR_6$—($CH_2$)$_2$-where $R_6$ is preferably methyl.

Preferably $R_2$ is hydrogen and $R_3$ is hydrogen or $C_{1-6}$ alkyl, for example methyl.

Most preferably $R_2$ and $R_3$ are hydrogen.

Suitable examples of pharmaceutical esters of the compounds of formula (I) include $C_{1-6}$ alkyl esters wherein the alkyl moiety is optionally substituted by up to three halo atoms selected from chloro, fluoro and bromo, such as methyl, ethyl, n- and iso-propyl, n-, iso-, sec- and tert-butyl and 2,2,2-trifluoroethyl esters, $C_{2-6}$ alkenyl esters such as vinyl, prop-1-enyl, prop-2-enyl, 1-methylvinyl, but-1-enyl, but-3-enyl, pent-4-enyl, 1-methylenepropyl and 1-methylprop-2-enyl, (in both their E and Z forms where stereoisomerism exists), $C_{2-6}$ alkynyl esters such as prop-2-ynyl, but-2-ynyl and but-3-ynyl, $C_{3-6}$ cycloalkyl esters such as cyclohexyl and $C_{3-6}$ cycloalkyl-$C_{1-4}$ alkyl esters such as cyclopropylmethyl, cyclopropylethyl and cyclobutylmethyl. Preferably the pharmaceutically acceptable ester is the methyl, ethyl, 2,2,2-trifluoroethyl, n-propyl, prop-2-enyl, prop-2-ynyl, but-3-enyl, but-2-ynyl, but-3-ynyl or cyclopropylmethyl ester, most preferably the but-2-ynyl or buty-3-ynyl ester, i.e. $R_4$ is methyl, ethyl, 2,2,2-trifluoroethyl, n-propyl, prop-2-enyl, prop-2-ynyl, but-3-enyl, but-2-ynyl, but-3-ynyl or cyclopropylmethyl, most preferably but-2-ynyl or but-3-ynyl.

Suitable values of $R_5$ include hydrogen, methyl, ethyl and n and iso propyl, preferably hydrogen. Alternatively, $R_5$ and $R_8$ together may represent an 8-(1-methylethylidene) group.

Values for $R_9$ include hydrogen and methyl. $R_9$ is preferably hydrogen.

There is a preferred group of compounds within formula (I) of formula (II) or a pharmaceutically acceptable salt thereof:

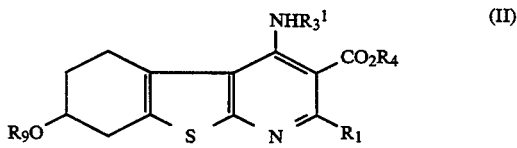

wherein $R_3^1$ is hydrogen or $C_{1-6}$ alkyl and $R_1$, $CO_2R_4$ and $R_9$ are as defined in formula (I).

Preferred values for $R_1$, $R_3^1$, $CO_2R_4$ and $R_9$ are as described for the corresponding variables in formula (I).

The compounds of the formula (I) can form acid addition salts with acids, such as the conventional pharmaceutically acceptable acids, for example, maleic, hydrochloric, hydrobromic, phosphoric, acetic, fumaric, salicylic, citric, lactic, mandelic, tartaric, methanesulphonic and oxalic acid.

It will be appreciated that the compounds of formula (I) in which $R_2$ or $R_3$ is hydrogen may exist tautomerically in more than one form. The invention extends to each of these forms and to mixtures thereof.

Compounds of formula (I) may also form solvates such as hydrates, and the invention also extends to these forms. When referred to herein, it is understood that the term "compound of formula (I)" also includes solvates thereof.

It should be appreciated that compounds of formula (I) have a chiral centre on the carbon atom adjacent to the $R_9O$ moiety and those in which $R_8$ is hydrogen and $R_5$ is other than hydrogen have a chiral centre on the carbon atom adjacent to the $R_5$ moiety. In addition, compounds in which $R_5$ and $R_8$ represent an alkylidene group may exist in E and Z forms, while substituents $R_1$, $R_2$, $R_3$, $R_4$, and $R_5$ may contain asymmetric carbon atoms. The present invention extends to any single stereoisomers such as enantiomers or diastereomers, or mixtures thereof including racemates, of compounds of formula (I).

The invention also provides a process for the preparation of a compound of formula (I), or a pharmaceutically acceptable salt thereof which process comprises the cyclisation of a compound of formula (III):

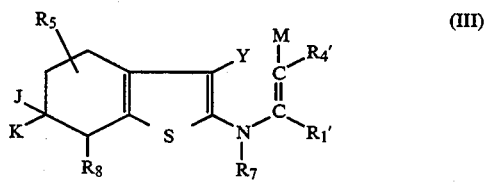

or imine tautomer thereof, wherein $R_1'$ is $R_1$ as defined in formula (I) or a group convertible thereto, $R_4'$ is $-CO_2R_4$ as defined in formula (I) or an electron-withdrawing group convertible to $-CO_2R_4$, $R_5$ and $R_8$ are as defined as in formula (I), $R_7$ is hydrogen or an N-protecting group, J and K together represent an optionally protected keto group, or J is hydrogen and K is $OR_9$ or a protected hydroxy group where $R_9$ is as defined in formula (I), Y is a group CN or $COL_1$, wherein $L_1$ is a leaving group and M is hydrogen, or Y is hydrogen and M is a group CN or $COL_2$, wherein $L_2$ is a leaving group; and thereafter, optionally or as necessary, and in any appropriate order, converting $R_7$ when hydrogen to an N-protecting group, when Y or M is a group $COL_1$ or $COL_2$, converting the resulting hydroxy group to a leaving group and reacting the latter with a compound $HNR_2'R_3'$ wherein $R_2'$ and $R_3'$ are $R_2$ and $R_3$ as defined in formula (I) or N-protecting groups, removing any $R_2'$, $R_3'$ or $R_7$ N-protecting group, converting any electron-withdrawing group $R_4'$ to $CO_2R_4$, converting $R_1'$ when other than $R_1$ to $R_1$, converting J and K to hydrogen and $OR_9$ respectively, interconverting $R_2$, $R_3$, $R_4$, $R_5$, $R_8$ and $R_9$, separating any stereoisomers such as enantiomers or diastereomers and/or forming a pharmaceutically acceptable salt of a compound of formula (I).

The cyclisation of the enamine of formula (III) or imine tautomer thereof may be carried out under conventional conditions, in the presence of a strong base such as an alkali metal alkoxide, for example sodium methoxide or sodium ethoxide in a suitable solvent such as methanol or ethanol, at elevated temperature, or in the presence of a Lewis acid such as $ZnCl_2$, $SnCl_4$ or $CuOCOCH_3$ in a suitable solvent such as n-butyl acetate at elevated temperature.

Lewis acid catalysed cyclisation using copper (I) acetate is preferred especially when cyclising to give compounds of formula (I) directly i.e. where $R_4'$ is $CO_2R_4$.

Preferably J and K together represent a protected keto group or K represents a protected hydroxy group. A protected hydroxy such as a silyl ether, for example trimethylsilyl ether, tetrahydropyranyl ether or $C_{1-6}$ alkyl or benzyl ester optionally substituted as described hereinafter for the protecting group Q when benzyl, may be de-protected conventionally to give a hydroxy group.

A protected keto group may be first converted to keto and then reduced to hydroxy using a suitable reducing agent such as sodium borohydride.

Protected keto groups J and K are exemplified by compounds of formula (III) wherein J is $XR_{13}$ and K is $ZR_{14}$, X and Z are independently oxygen or sulphur and $R_{13}$ and $R_{14}$ are independently $C_{1-6}$ alkyl or together are $C_{2-4}$ polymethylene optionally substituted with one or more $C_{1-6}$ alkyl groups.

When X and Z are both oxygen, the group $-X-R_{13}$ and $-Z-R_{14}$ may be conventionally converted to a keto group for example by treatment with aqueous hydrochloric, formic or trifluoroacetic acid.

When one of X or Z is an oxygen atom and the other is a sulphur atom, the group $-X-R_{13}$ and $-Z-R_{14}$ may be conventionally converted to a keto group, for example by treatment with aqueous hydrochloric acid or quaternisation of the sulphur atom followed by hydrolysis, for example using an alkyl halide followed by water.

When X and Z are both sulphur the group $-X-R_{13}$ and $-Z-R_{14}$ may be conventionally converted to a keto group by reacting one of the sulphur atoms with:
(i) a heavy metal cation such as silver; or
(ii) a quaternising agent such as an alkyl halide; or
(iii) an oxidising agent such as a peracetic acid; and thereafter, hydrolysing off the protecting group to afford a keto group, for example using aqueous acetone or aqueous acetonitrile.

Preferably X and Z are oxygen.

The hydroxy group $OR_9$ where $R_9$ is hydrogen may be converted to other $OR_9$ groups by conventional etherification reactions, for example by treatment with a strong base such as sodium hydride in an inert solvent such as dimethylformamide followed by reaction with the appropriate alkyl halide, preferably the iodide, bromide or chloride. Protection of the remaining substituents, particularly the 4-amino group, may be required.

Alternatively, the protected keto group where J is $OR_{13}$ and K is $OR_{14}$ may be cleaved with a reducing agent such as zinc borohydride and trimethylsilyl chloride. The cyclic ketal will give rise to a terminal hydroxy substituent on the alkyl ether which can be removed conventionally.

When J and K together represent a keto group, $R_5$ and $R_8$ hydrogen may be converted to an alkylidene group in the 8-position by an aldol condensation with an appropriate aldehyde or ketone, such as acetone. The alkylidene group may then be hydrogenated to the corresponding $R_5$ alkyl group conventionally using, for example, a palladium on charcoal catalyst.

Examples of $R_7$ N-protecting groups include trimethylsilyl and 2-(trimethylsilyl)ethoxymethyl, which may be removed conventionally, for example using tetra-n-butylammonium fluoride.

Preferably $R_7$ is hydrogen.

Suitable examples of groups $R_4'$ include the groups hereinbefore described for $-CO_2R_4$, $COR_a$ where $R_a$ is hydrogen, $C_{1-6}$ alkyl, $C_{3-7}$ cycloalkyl $C_{1-4}$ alkyl or $C_{3-7}$ cycloalkyl, CH=NOH, $CO_2H$, $CO_2Q$ where Q is a protecting group such as benzyl wherein the benzyl moiety is optionally substituted in the phenyl ring by one or two of halogen, $CF_3$, $C_{1-6}$ alkoxy, $C_{1-6}$ alkyl or nitro, cyano and $-CONR_{10}R_{11}$ where $R_{10}$ and $R_{11}$ are independently selected from hydrogen, $C_{1-6}$ alkyl, $C_{1-6}$ alkoxy and phenyl or phenyl $C_{1-4}$ alkyl optionally substituted as described above for optional substituents in the phenyl ring of a benzyl ester, or together form a $C_{2-6}$ polymethylene chain optionally interrupted by oxygen or $NR_{12}$ wherein $R_{12}$ is hydrogen or $C_{1-6}$, e.g. morpholino or piperazino.

A protecting group Q may be removed by conventional hydrolysis or hydrogenolysis to yield the free acid which can then be esterified under conventional conditions by reaction with the appropriate alcohol $R_4OH$, optionally with prior conversion of the acid to the acid chloride by reaction with a suitable chlorinating agent such as thionyl chloride, or with an alkylating agent $R_4X$ where X is a leaving group such as chloro, bromo or iodo, optionally in the presence of a suitable base such as potassium hydroxide or carbonate in an inert solvent such as dimethylformamide. Alternatively Q may be converted directly to $R_4$ by transesterification, under basic conditions.

An intermediate amide may be hydrolysed to the free acid which can then be esterified as described above.

An $R_4'$ cyano group may be converted under anhydrous acidic conditions to an imino ester by reaction with the appropriate alcohol $R_4OH$ and then hydrolysed to the group $-CO_2R_4$.

An $R_4'$ CH=NOH group may be converted to cyano by dehydration with a suitable dehydrating agent such as formic acid at elevated temperature, and the resulting cyano group converted to $CO_2R_4$ as just described. Alternatively the CH=NOH group may be converted to formyl by hydrolysis, oxidised to the free acid using a suitable oxidising agent such as $CrO_3$ and esterified as above.

$R_4'$ $COR_a$ α-methylene keto groups may be converted to $CO_2R_4$ via the acid by a haloform reaction and esterification.

$R_4$ groups may be interconverted via the intermediate acid or directly by transesterification as described above.

Suitable examples of a leaving groups $L_1$ and $L_2$ when Y or M is $COL_1$ or $COL_2$ include hydroxy and, more preferably, alkoxy such as $C_{1-6}$ alkoxy; for example ethoxy or methoxy. The cyclisation of the compound of formula (III) or imine tautomer thereof gives a resulting compound having an hydroxy group in the 4-position of the pyridine ring. The hydroxy group may be converted to a leaving group such as those defined below for L, preferably halo such as chloro, by reaction with a halogenating agent such as phosphorus oxychloride or phosphorus oxybromide. The leaving group may be displaced by the compound $HNR_2'R_3'$ under conventional conditions for nucleophilic aromatic displacements, at elevated temperatures in an inert solvent such as toluene, methanol, ethanol, dimethylformamide or dioxan. Alternatively, the reaction may be carried out in neat $HNR_2'R_3'$ which functions as the solvent.

An $R_2'$ or $R_3'$ protecting group such as p-methoxybenzyl may be removed conventionally.

Conversion of $R_2$ and $R_3$ hydrogen to other $R_2/R_3$ may be carried out in accordance with conventional procedures for the alkylation or acylation of a primary amine. Acylation may be carried out by reaction with the appropriate acyl halide. However, $R_2/R_3$ other than hydrogen or acyl groups are preferably introduced via the route in which Y or M is $COL_1$ or $COL_2$ in the compound of formula (III), by displacement of the leaving group with the compound $HNR_2'R_3'$ as discussed above.

An $R_1'$ group such as hydroxy or chloro may be converted to alkyl or phenyl $C_{1-4}$ alkyl or phenyl, by a palladium mediated anion coupling reaction (V. N. Kalinin, Synthesis 1992, 413).

Separation of diastereomers or enantiomers may be carried out conventionally, for example using chiral HPLC or enzymatic methods.

Pharmaceutically acceptable salts may be prepared conventionally by reaction with the appropriate acid or derivative.

Compounds of formula (III) may be prepared by the reaction of a compound of formula (IV):

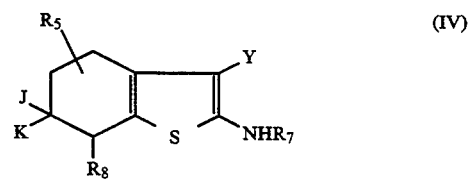
(IV)

with a compound of formula (V):

(V)

wherein $R_1'$, $R_4'$, $R_5$, $R_7$, $R_8$, Y, J, and K are as defined as in formula (III), L is a leaving group and M is as defined in formula (III) or L and M together represent a bond.

Novel intermediates of formula (III) and (IV) where J is $R_9O$ and K is hydrogen, $R_9$ being other than hydrogen, form a further aspect to the present invention.

Suitable examples of the leaving group L include halogens, such as chloro and bromo, hydroxy, $C_{1-6}$ acyloxy such as acetoxy, $C_{1-6}$ alkoxy, such as methoxy or ethoxy, preferably methoxy or $NR_bR_c$ where $R_b$ and $R_c$ are independently hydrogen of $C_{1-4}$ alkyl or together form a $C_{2-6}$ polymethylene chain optionally interrupted by oxygen or $NR_d$ where $R_d$ is hydrogen or $C_{1-6}$ alkyl optionally substituted by hydroxy. When L is hydroxy or a primary or secondary amino group, it will be appreciated that the compound of formula (V) exists in more than one tautomeric form.

The reaction of a compound of formula (IV) with a compound of formula (V) may be carried out under conditions conventional for condensation reactions, at elevated temperatures in an inert solvent such as toluene, benzene, ethanol, pyridine, dimethylformamide, mesitylene or dioxan, optionally in the presence of a catalyst such as para-toluene sulphonic acid or 10-camphorsulphonic acid, with water separation if appropriate.

For the preparation of compounds of formula (I) in which $R_1$ is hydrogen, the compound of formula (V) may be used in which:

(i) L and M together represent a bond or L is hydroxy and M is hydrogen, and $R_1'$ is a $C_{1-6}$ alkoxycarbonyl group. The reaction with the compound of formula (IV) may then be followed by a decarboxylation step to give $R_1$ hydrogen;

(ii) L is a leaving group and $R_1'$ is hydroxy. In the resulting compound, the $R_1'$ hydroxy may be converted to hydrogen by first replacing it by chloro by conventional chlorination with a chlorinating agent such as phosphorus oxychloride followed by reductive dehalogenation under conventional conditions, for example zinc in acetic acid. The conversion to $R_1$ hydrogen may be carried out before or, more preferably, after cyclisation of the compound of formula (III);

(iii) L is a leaving group, M and $R_4'$ are both $C_{1-6}$ alkoxycarbonyl, and $R_1'$ is hydrogen.

Compounds of formula (IV) are prepared analogously to the methods described in K. Gewald et al., Chem. Ber. 1966, 94, by reacting compounds of formula (VI):

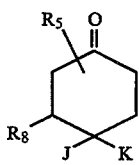

wherein $R_5$, $R_8$, J and K are as defined in formula (III), with $NCCH_2Y$ and sulphur in the presence of a base such as diethylamine in an inert solvent such as methanol or ethanol.

Compounds of formula (VI) are either known compounds or can be prepared analogously to known compounds.

Compounds of formula (V) are known compounds or can be prepared analogously to known compounds. For example, compounds of formula (V) wherein M is hydrogen, L is OH, $R_1'$ is $CH_3$ and $R_4'$ is $CO_2R_4$ may be prepared by reacting diketene with the appropriate alcohol $R_4OH$ using a method similar to that of R. J. Clemens and J. A. Hyatt, J. Org. Chem., 1985, 50,2431. The compound of formula (V) in which $R_1'$ is phenyl, M is hydrogen, L is ethoxy and $R_4'$ is ethoxycarbonyl is described by V. L. Leighton, Amer. Chem. Journal, 1898, 20, 133.

A class of intermediates comprises compounds of formula (VII) or a salt ester or amide thereof.

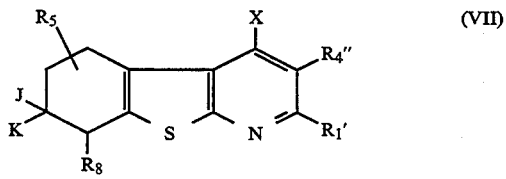

wherein $R_4''$ is $R_4'$ as defined in formula (III) or a group convertible to $CO_2R_4$, X is $NR_2'R_3'$, OH or chloro, $R_1'$, $R_2'$, $R_3'$, J and K are as defined in formula (III) and $R_4$, $R_5$ and $R_8$ are as defined in formula (I), provided that when X is $NR_2R_3$, J is hydrogen and K represents $OR_9$ and $R_1'$ is $R_1$, $R_4''$ is other than $CO_2R_4$. Novel compounds of formula (VII), for example where J is hydrogen and K is $R_9O$, $R_9$ being other than hydrogen, hereinafter referred to as compounds of formula (VIIa), also form part of the invention.

Examples of $R_4''$ when other than $CO_2R_4$ include $CO_2H$.

In a further aspect, the invention also provides a process for the preparation of a compound of formula (I) or a pharmaceutically acceptable salt thereof which process comprises deprotecting and/or reducing a compound of formula (VII) in which X is $NR_2R_3$, $R_4''$ is $CO_2R_4$ and $R_1'$ is $R_1$, wherein $R_1$, $R_2$, $R_3$, $—CO_2R_4$, $R_5$ and $R_8$ are as defined in formula (I) and J and K together represent a keto group or a group convertible thereto or a protected hydroxy group and thereafter optionally converting the hydroxy group to another $OR_9$ wherein $R_9$ is as defined in formula (I), optionally interconverting $R_2$, $R_3$, $R_4$, $R_5$, $R_8$ and/or $R_9$, optionally separating any stereoisomers such as diastereomers or enantiomers and/or forming a pharmaceutically acceptable salt of a compound of formula (I).

The present invention also provides a pharmaceutical composition, which comprises a compound of formula (I) or a pharmaceutically acceptable salt thereof, and a pharmaceutically acceptable carrier.

A pharmaceutical composition of the invention, which may be prepared by admixture, suitably at ambient temperature and atmospheric pressure, is usually adapted for oral or parenteral administration and, as such, may be in the form of tablets, capsules, oral liquid preparations, powders, granules, lozenges, reconstitutable powders, or injectable or infusable solutions or suspensions. Orally administrable compositions are generally preferred.

Tablets and capsules for oral administration may be in unit dose form, and may contain conventional excipients, such as binding agents, fillers, tabletting lubricants, disintegrants and acceptable wetting agents. The tablets may be coated according to methods well known in normal pharmaceutical practice.

Oral liquid preparations may be in the form of, for example, aqueous or oily suspension, solutions, emulsions, syrups or elixirs, or may be in the form of a dry product for reconstitution with water or other suitable vehicle before use. Such liquid preparations may contain conventional additives such as suspending agents, emulsifying agents, non-aqueous vehicles (which may include edible oils), preservatives, and, if desired, conventional flavourings or colourants.

For parenteral administration, fluid unit dosage forms are prepared utilising a compound of the invention or pharmaceutically acceptable salt thereof and a sterile vehicle. The compound, depending on the vehicle and concentration used, can be either suspended or dissolved in the vehicle. In preparing solutions, the compound can be dissolved for injection and filter sterilised before filling into a suitable vial or ampoule and sealing. Advantageously, adjuvants such as a local anaesthetic, preservatives and buffering agents are dissolved in the vehicle. To enhance the stability, the composition can be frozen after filling into the vial and the water removed under vacuum. Parenteral suspensions are prepared in substantially the same manner, except that the compound is suspended in the vehicle instead of being dissolved, and sterilization cannot be accomplished by filtration. The compound can be sterilised by exposure to ethylene oxide before suspension in a sterile vehicle. Advantageously, a surfactant or wetting agent is included in the composition to facilitate uniform distribution of the compound.

The composition may contain from 0.1% to 99% by weight, preferably from 10 to 60% by weight, of the active material, depending on the method of administration.

The dose of the compound used in the treatment of CNS disorders, such as anxiety, depression, sleep disorders or disorders treatable with anticonvulsant agents, such as epilepsy, will vary in the usual way with the seriousness of the disorder and the disorder itself, the weight of the sufferer, and other similar factors. However, as a general guide suitable unit doses may be 0.05 to 1000 mg, for anxiety more suitably 0.05 to 20.0 mg, for example 0.2 to 5 mg; and such unit doses may be administered more than once a day, for example two or three a day, so that the total daily dosage is in the range of about 0.01 to 100 mg/kg; and such therapy may extend for a number of weeks or months.

No unacceptable toxicological effects are expected when compounds of the invention are administered in accordance with the invention.

The invention further provides a pharmaceutical composition for use in the treatment of CNS disorders, in particular anxiety, depression, sleep disorders or disorders treatable with anticonvulsant agents, such as epilepsy, which composition comprises an effective, non-toxic amount of compound of formula (I) or a pharmaceutically acceptable salt thereof, and a pharmaceutically acceptable carrier.

The invention further provides a method for the treatment and/or prophylaxis of CNS disorders, in particular anxiety, depression, sleep disorders or disorders treatable with anticonvulsant agents, such as epilepsy, in mammals, including humans, which comprises administering to the sufferer an effective, non-toxic amount of a compound of formula (I) or a pharmaceutically acceptable salt thereof.

The invention also provides a compound of formula (I), or a pharmaceutically acceptable salt thereof for the use in the treatment and/or prophylaxis of CNS disorders, in particular anxiety, depression, sleep disorders or disorders treatable with anticonvulsant agents, such as epilepsy.

The invention yet further provides the use of a compound of formula (I), or a pharmaceutically acceptable salt thereof, in the manufacture of a medicament for treatment and/or prophylaxis of CNS disorders, in particular anxiety, depression, sleep disorders or disorders treatable with anticonvulsant agents, such as epilepsy.

The following examples illustrate the preparation of compounds of the invention.

DESCRIPTION 1

2-Amino-6,6-ethylenedioxy-4,5,6,7-tetrahydrobenzo[b]-thiophene-3carbonitrile carbonitrile (D1)

The title compound was prepared from 1,4-cyclohexanedione monoethylene ketal using a procedure similar to that of K. Gewald et al., Chem. Ber. 1966, 94 (49% yield). m.p. 190°–193° C. after recrystallization from methanol.

NMR (CDCl$_3$) δ: 1.95 (2H, t), 2.72 (4H, m), 4.02 (4H, s), 4.72 (2H, bs).

Found: C, 55.61; H, 5.22; N, 11.51%
C$_{11}$H$_{12}$N$_2$O$_2$S requires C, 55.91; H, 5.12; N, 11.86%

DESCRIPTION 2

N-3-(2-(3-Cyano-6,6-ethylenedioxy-4,5,6,7-tetrahydrobenzo[b]-thienyl)amino)-2-butenoic acid, ethyl ester (D2)

A mixture of aminonitrile D1 (13.16 g; 55.7 mmol)and ethyl bethoxycrotonate (26 g; 164 mmol) in mesitylene (400 ml) was heated at reflux for 1.5h then evaporated to dryness. The residue was chromatographed on Kieselgel 60 eluting with a 0–2% methanol in dichloromethane gradient. Trituration of the product with petrol (bpt: 40°–60° C.) and filtration afforded the title compound as a yellow solid (11.9g, 61%), m.p. 115°–118°C.

NMR (CDCl$_3$) δ: 1.30 (3H, t), 1.95 (2H, t), 2.10 (3H, s), 2.85 (4H, m), 4.02 (4H, s), 4.20 (2H, q), 4.90 (1H, s).

The title compound (D2) may also be prepared from the aminonitrile (D1) and 3-oxobutyric acid, ethyl ester by a procedure similar to that of Description 5.

DESCRIPTION 3

4-Amino-7,7-ethylenedioxy-2-methyl-5,6,7,8-tetrahydrobenzo[b]-thieno[2,3-b]pyridine-3-carboxylic acid, ethyl ester (D3)

Method A

A solution of enaminoester D2 (11.7 g, 33.6 mmol) in toluene (400 ml) was treated with a 1M solution of sodium ethoxide in ethanol (40 ml) and heated to reflux for 2.5 h. The reaction mixture was cooled and added to ethyl acetate and half-saturated aqueous ammonium chloride. The mixture was filtered, the organic phase separated, dried (Na$_2$SO$_4$) and evaporation in vacuo gave a brown oil. Chromatography on TLC alumina, eluting with a 0–2% methanol in dichloromethane gradient, afforded the title compound as a yellow gum (7 g, 60%).

NMR (CDCl$_3$) δ: 1.40 (3H, t), 2.05 (2H, t), 2.70 (3H, s), 3.00 (2H, s), 3.23 (2H, t), 4.05 (4H, s), 4.38 (2H, q), 6.60 (2H, bs).

Method B

A mixture of aminonitrile D1 (25 g; 106 mmol) and 3-oxobutyric acid, ethyl ester (16.5 g; 127 mmol) in toluene (1.2L) was warmed with stirring to give solution and then 10-camphorsulphonic acid (CSA) (2.5 g) added. The mixture was heated at reflux under Dean and Stark conditions for 1.5 h and then, after cooling, a 1M solution of sodium ethoxide in ethanol (125 ml; 1.2 equiv.) was added. Heating was continued for 2.25 h collecting the first 120 ml of distillate. The resulting dark brown solution was allowed to cool and then poured into water (1L) and ethyl acetate (250 ml) and the layers separated. The aqueous layer was further extracted with ethyl acetate (500 ml) and the combined organic layers then washed with brine, dried over anhydrous sodium sulphate and evaporated to dryness. This crude product was purified by chromatography on Kieselgel 60 eluting with a 30–50% ethyl acetate in pentane gradient to give the title compound as a yellow solid (21.29 g, 58%) having spectroscopic properties identical to material prepared by Description 3, Method A. A small sample was recrystallised from ethyl acetate/petrol (bpt: 40°–60° C.), m.p. 122° C.

As an alternative to purification by chromatography the crude product can be triturated with ethyl acetate to give the title compound as a yellow solid (43.2%).

Found: C, 58.62; H, 5.76; N, 8.04% C$_{17}$H$_{20}$N$_2$O$_4$S requires C, 58.60; H, 5.79; N, 8.04%

DESCRIPTION 4

4-Amino-2-methyl-7-oxo-5,6,7,8-tetrahydrobenzo[b]thieno[2,3-b]-pyridine-3-carboxylic acid, ethyl ester (D4)

A solution of ketal D3 (4.62 g, 13.3 mmol) in acetone (200 ml) was treated with water (10 ml) and concentrated hydrochloric acid (2 ml) then heated to reflux under nitrogen for 24h. Additional concentrated hydrochloric acid (2 ml) was added, and the mixture heated to reflux for 8 h, then stored at ca. 5° C. for 12h. Filtration afforded a white crystalline solid (3.5 g) which was partitioned between ethyl acetate and saturated aqueous sodium bicarbonate solution. The organic phase was separated, dried ($Na_2SO_4$) and concentrated in vacuo whereupon crystallisation occurred. After storing at ca. 5° C. for 12h, filtration afforded the title compound as a white crystalline solid (2.37 g, 59%), m.p. 159°–161° C.

NMR ($CDCl_3$) δ: 1.42 (3H, t), 2.71 (3H, s), 2.80 (2H, t), 3.45 (2H, t), 3.78 (2H, s), 4.40 (2H, q), 6.55 (2H, bs).

Found: C, 59.32; H, 5.19; N, 9.17% $C_{15}H_{16}N_2O_3S$ requires C, 59.19; H, 5.30; N, 9.20%

The deprotection may alternatively be carried out by the procedure of Description 16.

DESCRIPTION 5

N-3-(2-(3-Cyano-6,6-ethylenedioxy-4,5,6,7-tetrahydrobenzo[b]thienyl) amino)-2-butenoic acid, but-2-ynyl ester (D5)

The aminonitrile D1 (8.0 g, 34 mmol), 3-oxobutyric acid, but-2-ynyl ester (6.2 g, 40 mmol), CSA (0.8 g) and toluene (300 ml) were heated at reflux under a Dean and Stark apparatus for 1h. The reaction mixture was cooled and evaporated to dryness. The residue was chromatographed on Kieselgel 60 eluting with dichloromethane to afford the title compound as a yellow solid (8.9 g, 70%).

NMR ($CDCl_3$) δ: 1.86 (3H, t), 1.96 (2H, t), 2.10 (3H, s), 2.82 (2H, t), 2.86 (2H, s), 4.04 (4H, s), 4.73 (2H, q), 4.94 (1H, s), 10.88 (1H, s).

DESCRIPTION 6

N-3-(2-(3-Cyano-6,6-ethylenedioxy-4,5,6,7-tetrahydrobenzo[b]thienyl) amino)-2-butenoic acid, cyclobutylmethyl ester (D6)

The title compound was prepared from the aminonitrile D1 and 3-oxobutyric acid, cyclobutylmethyl ester by a procedure similar to that of Description 5.

NMR ($CDCl_3$) δ: 1.70–2.15 (11H, bm), 2.65 (1H, m), 2.82 (2H, t), 2.86 (2H, s), 4.04 (4H, s), 4.13 (2H, t), 4.90 (1H, s), 10.98 (1H, s).

DESCRIPTION 7

N-3-(2-(3-Cyano-6,6-ethylenedioxy-4,5,6,7-tetrahydrobenzo[b]thienyl)amino)-2-butenoic acid, cyclopropylmethyl ester (D7)

The title compound was prepared from the aminonitrile D1 and 3-oxobutyric acid, cyclopropylmethyl ester by a procedure similar to that of Description 5 as a yellow gum (98%) after chromatography on Kieselgel 60. This solidified on standing. m/z=374(M+)

DESCRIPTION 8

N-3-(2-(3-Cyano-6,6-ethylenedioxy-4,5,6,7-tetrahydrobenzo[b]thienyl)amino)-2-butenoic acid, methyl ester (D8)

The title compound was prepared from aminonitrile D1 and 3-oxobutyric acid, methyl ester, by a procedure similar to that of Description 5, as a pale yellow solid (55%)

DESCRIPTION 9

4-Amino-7,7-ethylenedioxy-2-methyl-5,6,7,8-tetrahydrobenzo[b]thieno[2,3-b]pyridine-3-carboxylic acid, but-2-ynyl ester (D9)

The enamine D5 (1.8 g, 4.8 mmol) and copper (I) acetate (200 mg) in n-butyl acetate (40 ml) were heated under reflux for 0.5h. The reaction mixture was cooled and filtered through Kieselguhr. Ethyl acetate (100 ml) was added and the solution was washed with aqueous ammonium hydroxide then brine. The organic solution was dried over sodium sulphate and evaporated to dryness. The residue was chromatographed on Kieselgel 60 eluting with 30% ethyl acetate/pentane to give the title compound as a yellow solid (1.1 g, 61%), m.p. 148°–149° C.

NMR ($CDCl_3$) δ: 1.88 (3H, t), 2.05 (2H, t), 2.74 (3H, s), 3.02 (2H, s), 3.23 (2H, t), 4.06 (4H, s), 4.88 (2H, q), 6.60 (2H, bs).

Found: C, 61.36; H, 5.38; N, 7.46% $C_{19}H_{20}N_2O_4S$ requires C, 61.27; H, 5.41; N, 7.52%

DESCRIPTION 10

4-Amino-7,7-ethylenedioxy-2-methyl-5,6,7,8-tetrahydrobenzo[b]-thieno[2,3-b]pyridine-3-carboxylic acid, cyclobutylmethyl ester (D10)

The title compound was prepared in 43% yield from enamine D6 by a produre similar to that outlined in Description 9, m.p. 115°–116° C.

NMR ($CDCl_a$) δ: 1.75–2.23 (8H, bm), 2.68 (3H, s), 2.78 (1H, m), 3.02 (2H, s), 3.23 (2H, t), 4.05 (4H, s), 4.30 (2H, d), 6.61 (2H, bs).

Found: C, 61.66; H, 6.15; N, 7.02% $C_{20}H_{24}N_2O_4S$ requires C, 61.84; H, 6.23; N, 7.02%

DESCRIPTION 11

4-Amino-2-methyl-7,7-ethylenedioxy-5,6,7,8-tetrahydrobenzo[b]-thieno[2,3-b]pyridine-3-carboxylic acid, cyclopropylmethyl ester (D11)

The enamine D7 was cyclized by a procedure similar to that of Description 9 to give the title compound as a pale yellow gum (65%) which solidified on standing. A small portion was recrystallised from ethyl acetate/pentane to give a white crystalline solid, m.p. 115°–116.5° C.

NMR ($CDCl_3$) δ: 0.38 (2H, m), 0.65 (2H,m), 1.27 (1H, m), 2.05 (2H, t), 2.74 (3H, s), 3.01 (2H, s), 3.22 (2H, t), 4.06 (4H, s), 4.15 (2H, d), 6.54 (2H, bs).

Found: C, 61.19; H, 5.83; N, 7.53% $C_{19}H_{22}N_2O_4S$ requires C, 60.94; H, 5.92; N, 7.48%

DESCRIPTION 12

4-Amino-2-methyl-7,7-ethylenedioxy-5,6,7,8-tetrahydrobenzo[b]thieno[2,3-b]pyridine-3-carboxylic acid, methyl ester (D12)

The enamine D8 was cyclized with copper (I) acetate by a procedure similar to that of Description 9 to give the title compound as pale yellow flakes (42%) after recrystallization from ethyl acetate/pentane, m.p. 140°–141.5° C.

NMR (CDCl$_3$) δ: 2.07 (2H, t), 2.69 (3H, s), 3.02 (2H, s), 3.23 (2H, t), 3.92 (3H, s), 4.07 (4H, s), 6.60 (2H, bs).

Found: C, 57.46; H, 5.46; N, 8.41% C$_{16}$H$_{18}$N$_2$O$_4$S requires C, 57.47; H, 5.43; N, 8.38% m/z=334(M+)

DESCRIPTION 13

4-Amino-7,7-ethylenedioxy-2-methyl-5,6,7,8-tetrahydrobenzo[b]thieno[2,3-b]pyridine-3-carboxylic acid, prop-2-ynyl ester (D13)

Ester D3, Method B, (4.3 g, 12 mmol) and potassium hydroxide (2.0 g, 36 mmol) in methanol/H$_2$O (80 ml / 9 ml) were heated under reflux for 24h. The reaction mixture was cooled and evaporated to dryness. The residue was dissolved in dimethylformamide (100 ml). Propargyl bromide (1.7 ml, 80 wt% in toluene) was added and the mixture was stirred at room temperature for 2h. It was necessary to add a further portion of propargyl bromide (1.7 ml). After stirring for a further 2h, water (100 ml) was added. The aqueous solution was extracted with ethyl acetate. The combined organics were washed with brine, dried and evaporated. The residue was chromatographed on Kieselgel 60 eluting with 30% ethyl acetate/pentane to give the title compound as a yellow solid (3.6 g, 81%). A sample was crystallised from ethyl acetate, m.p. 128°–129° C.

NMR (CDCl$_3$) δ: 2.06 (2H, t), 2.54 (1H, t), 2.74 (3H, s), 3.00 (2H, s), 3.22 (2H, t), 4.06 (4H, s), 4.94 (2H, d), 6.63 (2H, bs).

Found: C, 60.37; H, 5.08; N, 7.90% C$_{18}$H$_{18}$N$_2$O$_4$S requires C, 60.32; H, 5.06; N, 7.82%

DESCRIPTION 14

4-Amino-7,7-ethylenedioxy-2-methyl-5,6,7,8-tetrahydrobenzo[b]thieno[2,3-b]pyridine-3-carboxylic acid, but-3-ynyl ester (D14)

The title compound was prepared in a yield of 88% by a procedure similar to that outlined in Description 13, m.p. 154°–155° C.

NMR (CDCl$_3$) δ: 2.07 (3H, m), 2.69 (2H, dt), 2.75 (3H, s), 3.02 (2H, s), 3.23 (2H, t), 4.07 (4H, s), 4.45 (2H, t), 6.63 (2H, bs).

Found: C, 61.34; H, 5.34; N, 7.59% C$_{19}$H$_{20}$N$_2$O$_4$S requires C, 61.27; H, 5.41; N, 7.52%

DESCRIPTION 15

4-Amino-7,7-ethylenedioxy-2-methyl-5,6,7,8-tetrahydrobenzo[b]thieno[2,3-b]pyridine-3-carboxylic acid, but-3-enyl ester (D15)

The title compound was prepared in a yield of 83% by a procedure similar to that outlined in Description 13, m.p. 100°–101° C.

NMR (CDCl$_3$) δ: 2.06 (2H, t), 2.55 (2H, m), 2.70 (3H, s), 3.00 (2H, s), 3.22 (2H, t), 4.06 (4H, s), 4.39 (2H, t), 5.10–5.26 (2H, bm), 5.77–5.97 (1H, bm), 6.57 (2H, bs).

Found: C, 60.79; H, 5.83; N, 7.31%
C$_{19}$H$_{22}$N$_2$O$_4$S requires C, 60.94; H, 5.92; N, 7.48%

DESCRIPTION 16

4-Amino-2-methyl-7-oxo-5,6,7,8-tetrahydrobenzo[b]-thieno[2,3-b]-pyridine-3-carboxylic acid, but-2-ynyl ester (D16)

The ester, D9 (3.48 g, 9.4 mmol) was stirred in trifluoroacetic acid/water (18 ml/1 ml) for 18h. The reaction mixture was added dropwise with ice-cooling to a solution of potassium carbonate (18 g) in H$_2$O (50 ml). The aqueous mixture was extracted with ethyl acetate. The combined organic extracts were washed with brine and dried over sodium sulphate. Evaporation to dryness afforded the title compound as a pale yellow solid (2.6 g, 84%). A small sample was crystallised from ethyl acetate, m.p. 190°–192° C.

NMR (CDCl$_3$) δ: 1.90 (3H, t), 2.76 (3H, s), 2.83 (2H, t), 3.47 (2H, t), 3.67 (2H, s), 4.92 (2H, q), 6.60 (2H, bs).

Found: C, 62.16; H, 4.89; C, 8.55% C$_{17}$H$_{16}$N$_2$O$_3$S requires: C, 62.18; H, 4.91; N, 8.53%

The deprotection could also be carried out by a procedure similar to the above substituting formic acid for trifluoroacetic acid.

DESCRIPTION 17

4-Amino-2-methyl-7-oxo-5,6,7,8-tetrahydrobenzo[b]-thieno[2,3-b]-pyridine-3-carboxylic acid, cyclobutylmethyl ester (D17)

The title compound was prepared from the ketal D10 in 85% yield by a procedure similar to that outlined in Description 16, m.p. 170°–172° C.

NMR (CDCl$_3$) δ: 1.75–2.25 (6H, bm), 2.71 (3H, s), 2.81 (3H, m), 3.44 (2H, t), 3.66 (2H, s), 4.30 (2H, d), 6.56 (2H, bs).

Found: C, 62.56; H, 5.75; N, 8.27% C$_{18}$H$_{20}$N$_2$O$_3$S requires C, 62.77; H, 5.85; N, 8.13%

DESCRIPTION 18

4-Amino-2-methyl-7-oxo-5,6,7,8-tetrahydrobenzo[b]-thieno[2,3-b]-pyridine-3-carboxylic acid, cyclopropylmethyl ester (D18)

The title compound was prepared from the ketal D11 by a procedure similar to that of Description 16 as a pale yellow solid (93%).

NMR (CDCl$_3$) δ: 0.38 (2H, m), 0.67 (2H, m), 1.28 (1H, m), 2.77 (3H, s), 2.81 (2H, t), 3.44 (2H, t), 3.67 (2H, s), 4.18 (2H, d), 6.59 (2H, bs).

DESCRIPTION 19

4-Amino-2-methyl-7-oxo-5,6,7,8-tetrahydrobenzo[b]-thieno[2,3-b]-pyridine-3-carboxylic acid, methyl ester (D19)

The ketal D12 was converted to the tifle compound with trifluoroacetic acid by a similar procedure to that of Description 16 and after recrystallisation from chloroform/pentane was obtained as a pale yellow solid (78%), m.p. 202°–207° C.

NMR (CDCl$_3$) δ: 2.70 (3H, s), 2.80 (2H, t), 3.45 (2H, t), 3.67 (2H, s), 3.93 (3H, s), 6.55 (2H, bs).

Found: C, 57.62; H, 4.81; N, 9.69% C$_{14}$H$_{14}$N$_2$O$_3$S requires C, 57.92; H, 4.86; N, 9.65%

DESCRIPTION 20

4-Amino-2-methyl-7-oxo-5,6,7,8-tetrahydrobenzo[b]-thieno[2,3-b]-pyridine-3-carboxylic acid, prop-2-ynyl ester (D20)

The title compound was prepared from the ketal D13 in 98% yield by a procedure similar to that outlined in Description 16, m.p. 196°–198° C.

NMR (CDCl$_3$) δ: 2.56 (1H, t), 2.78 (3H, s), 2.88 (2H, t), 3.46 (2H, t), 3.68 (2H, s), 4.95 (2H, d), 6.64 (2H, bs).

Found: C, 61.16; H, 4.52; N, 9.12% C$_{16}$H$_{14}$N$_2$O$_3$S requires C, 61.13; H, 4.49; N, 8.91%

DESCRIPTION 21

4-Amino-2-methyl-7-oxo-5,6,7,8-tetrahydrobenzo[b]-thieno[2,3-b]-pyridine-3-carboxylic acid, but-3-ynyl ester (D21)

The title compound was prepared from the ketal D14 in 87% yield by a procedure similar to that outlined in Description 16, m.p. 176°–178° C.

NMR (CDCl$_3$) δ: 2.07 (1H, t), 2.68 (2H, dt), 2.76 (3H, s), 2.82 (2H, t), 3.46 (2H, t), 3.67 (2H, s), 4.46 (2H, t), 6.50 (2H, bs).

Found: C, 62.32; H, 4.94; N, 8.64% C$_{17}$H$_{16}$N$_2$O$_3$S requires C, 62.18; H, 4.91; N, 8.53%

DESCRIPTION 22

4-Amino-2-methyl- 7-oxo-5,6,7,8-tetrahydrobenzo[b]-thieno[2,3-b]-pyridine-3-carboxylic acid, but-3-enyl ester (D22)

The title compound was prepared from the ketal D15 in a yield of 85% by a procedure similar to that outlined in Description 16, m.p. 130°–132° C.

NMR (CDCl$_3$) δ: 2.56 (2H, m), 2.72 (3H, s), 2.81 (2H, t), 3.45 (2H, t), 3.67 (2H, s), 4.42 (2H, t), 5.00–5.26 (2H, bm), 5.78–5.98 (1H, bm), 6.55 (2H, bs).

Found: C, 61.59; H, 5.51; N, 8.55% C$_{17}$H$_{18}$N$_2$O$_3$S requires C, 61.80; H, 5.49; N, 8.48%

DECRIPTION 23

4-Amino-7,7-ethylenedioxy-2-methyl-5,6,7,8-tetrahydrobenzo[b]-thieno[2,3-b]pyridine-3-carboxylic acid, propyl ester (D23)

The title compound was prepared in 71% yield from the ester D3 by a procedure similar to that outlined in Description 13, m.p. decomposes above 85° C.

NMR (CDCl$_3$) δ: 1.05 (3H, t), 1.80 (2H, m), 2.07 (2H, t), 2.73 (3H, s), 3.00 (2H, s), 3.22 (2H, t), 4.06 (4H, s), 4.28 (2H, t), 6.62 (2H, bs).

Found: C, 59.48; H, 6.04; N, 7.70% C$_{18}$H$_{22}$N$_2$O$_4$S requires C, 59.65; H, 6.12; N, 7.73%

DESCRIPTION 24

4-Amino-7,7-ethylenedioxy-2-methyl-5,6,7,8-tetrahydrobenzo[b]thieno[2,3-b]pyridine-3-carboxylic acid, (2-methyl) propyl ester (D24)

The title compound was prepared in 93% yield from the ester D3 by a procedure similar to that outlined in Description 13, m.p. 95°–97° C.

NMR (CDCl$_3$) δ: 1.04 (6H, d), 1.97–2.20 (3H, bm), 2.72 (3H, s), 3.03 (2H, s), 3.23 (2H, t), 4.05 (4H, s), 4.13 (2H, d), 6.64 (2H, bm).

Found: C, 60.60; H, 6.38; N, 7.35% C$_{19}$H$_{24}$N$_2$O$_4$S requires C, 60.62; H, 6.43; N, 7.44%

DESCRIPTION 25

4-Amino-2-methyl-7-oxo-5,6,7,8-tetrahydrobenzo[b]-thieno[2,3-b]-pyridine-3-carboxylic acid, propyl ester (D25)

The title compound was prepared from the ketal D23 in quantitative yield by a procedure similar to that outlined in Description 16.

NMR (CDCl$_3$) δ: 1.06 (3H, t), 1.85 (2H, m), 2.73 (3H, s), 2.82 (2H, t), 3.45 (2H, t), 3.70 (2H, s), 4.33 (2H, t), 6.58 (2H, bm).

DESCRIPTION 26

4-Amino-2-methyl-7-oxo-5,6,7,8-tetrahydrobenzo[b]-thieno[2,3-b]-pyridine-3-carboxylic acid, (2-methyl)propyl ester (D26)

The title compound was prepared from the ketal D24 in quantitative yield by a procedure similar to that outlined in Description 16, m.p. 186°–188° C.

NMR (CDCl$_3$) δ: 1.03 (6H, d), 2.12 (1H, m), 2.76 (3H, s), 2.82 (2H, t), 3.44 (2H, t), 3.68 (2H, s), 4.17 (2H, d), 6.65 (2H, bs).

Found: C, 61.14; H, 6.00; N, 8.44% C$_{17}$H$_{20}$N$_2$O$_3$S requires C, 61.42; H, 6.06; N, 8.43%

DESCRIPTION 27

4-Amino-7,7-ethylenedioxy-2-phenyl-5,6,7,8-tetrahydrobenzo[b]thieno[2,3-b]pyridine-3-carboxylic acid, ethyl ester (D27)

The title compound was prepared in 29% yield from the aminonitrile D1 and ethyl β-ethoxy cinnamate by a procedure similar to that of Description 3, method B, m.p. 114°–116° C.

NMR (d$_6$-DMSO) δ: 0.71 (3H, t), 1.89–2.03 (2H, bt), 2.93–3.03 (2H, bs), 3.13–3.27 (2H, bt), 3.92 (2H, q), 3.98 (4H, s), 6.46–6.59 (2H, bs), 7.40 (5H, s).

Found: C, 63.97; H, 5.43; N, 6.80% C$_{22}$H$_{22}$N$_2$O$_4$S requires C, 64.37; H, 5.40; N, 6.82%

DESCRIPTION 28

4-Amino-7-oxo-2-phenyl-5,6,7,8-tetrahydrobenzo[b]-thieno[2,3-b]-pyridine-3-carboxylic acid, ethyl ester (D28)

The title compound was prepared from the ketal D27 in 70% yield using a procedure similar to that in Description 16, m.p. 171°–172° C.

NMR (CDCl$_3$) δ: 0.73 (3H, t), 2.83 (2H, t), 3.49 (2H, t), 3.65–3.73 (2H, bs), 3.94 (2H, q), 6.14–6.30 (2H, bs), 7.31–7.52 (5H, m).

Found: C, 65.51; H, 5.03; N, 7.63% C$_{20}$H$_{18}$N$_2$O$_3$S requires C, 65.56; H, 4.95; N, 7.64%

DESCRIPTION 29

4-Amino-7,7-ethylenedioxy- 2- methyl-5,6,7,8-tetrahydrobenzo[b]-thieno[2,3-b]pyridine-3-carboxylic acid, pent-4-enyl ester (D29)

The ethyl ester, D3 (1.0 g; 2.87 mmol), was heated in 4-penten-1-ol (4 ml) until dissolution was complete, then sodium hydride (80% dispersion in mineral oil, 6 mgs) was added. The reaction mixture was then heated under nitrogen in an oil bath at 150° C. for 4 h, cooled, poured onto dilute brine and extracted with ethyl acetate. The combined organic extracts were washed with saturated brine, dried (Na$_2$SO$_4$) and evaporated to dryness. The residue was chromatographed on Kieselgel 60, eluting with a 0–50% ethyl acetate in pentane gradient. Recrystallisation from ethanol afforded white crystals (0.78 g, 70%), m.p. 93°–94° C.

NMR (CDCl$_3$) δ1.90 (2H, m), 2.06 (2H, t), 2.23 (2H, m), 2.71 (3H, s), 3.01 (2H, s), 3.23 (2H, t), 4.06 (4H, s), 4.34 (2H, t), 5.06 (2H, m), 5.83 (1H, m), 6.60 (2H, bs).

Found: C, 61.46; H, 6.14; N, 7.13% C$_{20}$H$_{24}$N$_2$O$_4$S requires C, 61.84; H, 6.23; N, 7.21%

DESCRIPTION 30

4-Amino-2-methyl-7-oxo-5,6,7,8-tetrahydrobenzo[b]-thieno[2,3-b]-pyridine-3-carboxylic acid, pent-4-enyl ester (D30)

The title compound was prepared from the ketal D29 (0.97 g) in 93% yield by a procedure similar to that outlined in Description 16 as an off-white solid (0.80 g).

NMR (CDCl$_3$) δ: 1.90 (2H, m), 2.23 (2H, m), 2.73 (3H, s), 2.82 (2H, t), 3.46 (2H, t), 3.68 (2H, s), 4.37 (2H, t), 5.06 (2H, m), 5.84 (1H, m), 6.58 (2H, bs).

DESCRIPTION 31

N-3-(2-(3-Cyano-6,6-ethylenedioxy-4,5,6,7-tetrahydrobenzo[b]-thienyl)amino)-2-butenoic acid, cyclohexyl ester (D31)

The title compound was prepared in 70% yield from the aminonitrile D1 and 3-oxobutyric acid, cyclohexyl ester, by a procedure similar to that outlined in Description 5.

NMR(CDCl$_3$) δ: 1.10–2.00 (12H, bm), 2.10 (3H,s), 2.84 (4H, m), 4.05 (4H, s), 4.86 (2H, m), 11.03 (1H, bs).

DESCRIPTION 32

4-Amino-7,7-ethylenedioxy-2-methyl-5,6,7,8-tetrahYdrobenzo[b]-thieno[2,3-b]pyridine-3-carboxylic acid, cyclohexyl ester (D32)

The title compound was prepared in 38% yield from the enamine D31 by a procedure similar to that outlined in Description 9.

NMR (CDCl$_3$) δ: 1.20–2.10 (12H, bm), 2.71 (3H, s), 3.01 (2H, s), 3.22 (2H, t,), 4.05 (4H, s), 5.07 (1H, m), 6.58 (2H, bs).

Description 33

4-Amino-2-methyl-7-oxo-5,6,7,8-tetrahydrobenzo[b]-thieno [2,3-b]pyridine-3-carboxylic acid, cyclohexyl ester (D33)

The title compound was prepared in 82% yield from the ester D32 by a procedure similar to that outlined in Description 16, m.p. 175°–6° C.

NMR (CDCl$_3$) δ: 1.20–2.10 (10H, bm), 2.73 (3H, s), 2.82 (2H, t,), 3.44 (2H, t,), 3.19 (2H, s), 5.09 (1H, m), 6.52 (2H, bs).

Found: C, 63.45; H, 6.13; N, 7.69% C$_{19}$H$_{22}$N$_2$O$_3$S requires: C, 63.66; H, 6.19; N, 7.81%

Description 34

4-Amino-2-ethyl-7,7-ethylenedioxy-5,6,7,8-tetrahydrobenzo[b]thieno[2,3-b]pyridine-3-carboxylic acid, ethyl ester, hemi-tartrate (D34)

The title compound was prepared in 20% yield from the aminonitrile D1 and 3-oxopentanoic acid, ethyl ester by a procedure similar to that outlined in Description 3, method B, m.p. 144°–146° C.

NMR (d$_6$-DMSO) δ: 1.17 (3H, t), 1.32 (3H, t), 1.87–2.01 (2H, bm), 2.80 (2H, q), 2.89–2.98 (2H, bs), 3.07–3.19 (2H, bt), 3.97 (4H, s), 4.32 (2H, s), 4.34 (2H, q), 6.36–6.51 (2H, bm).

Description 35

4-Amino-2-ethyl-7-oxo-5,6,7,8-tetrahydrobenzo[b]-thieno[2,3-b]pyridine-3-carboxylic acid, ethyl ester (D35)

The title compound was prepared in 81% yield from the ketal D34 using a procedure similar to that outlined in Description 16. NMR (CDCl$_3$) δ: 1.32 (3H, t), 1.43 (3H, t), 2.80 (2H, t), 3.06 (2H, q), 3.43 (2H, t), 3.60–3.71 (2H, bs), 4.41 (2H, q), 6.57 (2H, bs).

Description 36

N-3-(2-(3-Cyano-6,6-ethylenedioxy-4,5,6,7-tetrahydrobenzo[b]thienyl)amino)-2-butenoic acid, cyclopropylethyl ester (D36)

The title compound was prepared from aminonitrile D1 and 3-oxobutyric acid, cyclopropylethyl ester by a method similar to that of Description 5. A portion of the product was rechromatographed on silica with a gradient of 30–50% diethyl ether/pentane as eluant to remove 3-oxobutyric acid, cyclopropylethyl ester. m/z=388(M$^+$)

Description 37

4-Amino-7,7-ethylenedioxy-2-methyl-5,6,7,8-tetrahydrobenzo[b]thieno[2,3-b]pyridine-3-carboxylic acid, cyclopropylethyl ester (D37)

The title compound was prepared in 68% yield from D36 by a method similar to that of Description 9 as a pale yellow gum which slowy solidified on standing, m.p. 94°–96.5° C.

NMR(CDCl$_3$) δ: 0.12 (2H, m), 0.50 (2H, m), 0.82 (1H, m), 1.68 (2H, m), 2.05 (2H, t), 2.70 (3H, s), 3.01 (2H, s), 3.22 (2H, t), 4.06 (4H, s), 4.39 (2H, t), 6.60 (2H, bs)

MS measured 388.1460, calculated for C$_{20}$H$_{24}$N$_2$O$_4$S 388.1456.

Description 38

4-Amino-2-methyl-7-oxo-5,6,7,8-tetrahydrobenzo[b]-thieno[2,3.b] pyridine-3-carboxylic acid, cyclopropylethyl ester (D38)

The title compound was prepared in quantitative yield from the ketal D37 by a method similar to that of Description 16 as a yellow solid and was used without further purification.

NMR (CDCl$_3$) δ: 0.14 (2H, m), 0.51 (2H, m), 0.82 (1H, m), 1.69 (2H, m), 2.74 (3H, s), 2.81 (2H, t), 3.43 (2H, t), 3.68 (2H, s), 4.40 (2H, t), 6.60 (2H, bs)

MS measured 344.1165, calculated for C$_{18}$H$_{20}$N$_2$O$_3$S 334.1194

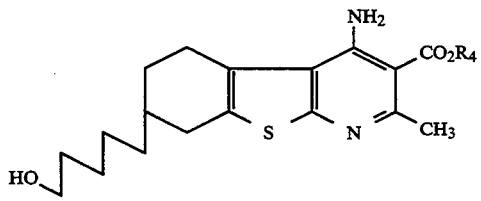

EXAMPLE 1

(±)-4-Amino-7-hydroxy-2-methyl-5,6,7,8-tetrahydrobenzo[b]thieno[2,3-b]pyridine-3-carboxylic acid, ethyl ester (E1, R$_4$=C$_2$H$_5$)

A solution of ethyl ester D4 (0.5 g; 1.6 mM) in ethanol (25 ml) was treated with sodium borohydride (0.03 g; 0.82 mM). After 1 h the reaction mixture was added to water (ca. 200 ml) and 5M aqueous hydrogen chloride added until pH3 was attained. Aqueous sodium bicarbonate was added, and the neutral mixture extracted with ethyl acetate. The combined ethyl acetate extracts were washed with brine, dried over sodium sulphate and evaporated to dryness. Recrystallisation from ethanol afforded the title compound (E1) as a white crystalline solid (0.18 g, 36%), m.p. 191° C.

NMR (CDCl$_3$) δ: 1.45 (3H, t), 1.85–2.20 (3H, bm), 2.75 (3H, s), 2.85 (1H, m), 3.00–3.25 (3H, bm), 4.30 (1H, bs), 4.40 (2H, q), 6.65 (2H, bs).

Found: C, 58.66; H, 5.90; N, 9.03% C$_{15}$H$_{18}$N$_2$O$_3$S requires C, 58.80; H, 5.92; N, 9.14%

EXAMPLE 2

(−)-4-Amino-7-hydroxy-2-methyl-5,6,7,8-tetrahydrobenzo[b]thieno[2,3-b]pyridine-3-carboxylic acid, ethyl ester (E2, R$_4$=C$_2$H$_5$)

The title compound was obtained from racemic E1 by preparative H.P.L.C. using the following conditions:
Column: Chiralcel OC, 250×20 mm.
Mobile Phase: 10/90=Ethanol/Hexane
Flow rate: 8 ml/min
Detection: U.V. at 250 nm
Sample concentration: 5 mg/ml
Sample injections: 1 ml.

The retention time of this enantiomer under these conditions was 55 minutes. The sample was recrystallised from ethanol, m.p. 168–170° C.

[α]$_D^{26}$= −54.89 (c=0.58, CHCl$_3$)

Found: C, 58.76; H, 5.94; N, 8.73% C$_{15}$H$_{18}$N$_2$O$_3$S requires C, 58.80; H, 5.92; N, 9.14%

EXAMPLE 3

(+)-4-Amino-7-hydroxy-2-methyl-5,6,7,8-tetrahydrobenzo[b]thieno[2,3-b]pyridine-3-carboxylic acid, ethyl ester (E3, R$_4$=C$_2$H$_5$)

The title compound was obtained from racemic E1 by preparative H.P.L.C. using the following conditions:
Column: Chiralcel OC, 250×20 mm
Mobile Phase: 10/90=Ethanol/Hexane
Flow rate: 8 ml/min
Detection: U.V. at 250 nm
Sample concentration: 5 mg/ml
Sample injections: 1 ml The retention time of this enantiomer under these conditions was 66 minutes. The sample was recrystallised from ethanol. m.p. 171–3° C.

[α]$_D^{26}$=52.17 (c=0.53, CHCl$_3$)

Found: C, 58.70; H, 5.85; N, 9.19% C$_{15}$H$_{18}$N$_2$O$_3$S requires C, 58.80; H, 5.92; N, 9.14%

EXAMPLES 2 and 3

Method B (−)-4-Amino-7-hydroxy-2-methyl-5,6,7,8-tetrahydrobenzo[b]thieno[2,3-b]pyridine-3-carboxylic acid, ethyl ester (E2, R$_4$=C$_2$H$_5$)

(+)-4-Amino-7-hydroxy-2-methyl-5,6,7,8-tetrahydrobenzo[b]thieno[2,3-b]pyridine-3-carboxylic acid, ethyl ester (E3, R$_4$=C$_2$H$_5$)

The ester E1 (4.47 g, 14.59 mM) was suspended in a mixture of vinyl acetate (450 ml) and di-isopropyl ether (450 ml) containing 1% (v/v) water. Pseudomonas fluorescens lipase (2 g) was added and the reaction mixture stirred at ambient temperature. The course of the reaction was monitored by HPLC [Silica gel column, 244 nm, 20% isopropyl alcohol in hexane and pump rate 2 ml/min.] against an authentic sample of the acetate. On reaching 40% acylation (approx. 3 h) the reaction mixture was diluted with chloroform (500 ml), dried over anhydrous Na$_2$SO$_4$ and evaporated under reduced pressure. The residual mixture of alcohol and acetate was separated by silica gel column chromatography eluting with ethyl acetate/hexane. The acetate was then hydrolysed in 0.1M K$_2$HPO$_4$/KH$_2$PO$_4$ buffer (pH7) containing 10% acetone to yield, after recrystallisation from ethanol, enantiomerically pure E3. The unreacted alcohol from the column could be re-enzymated to the point of 20% acylation, and worked up to yield enantiomerically pure E2.

EXAMPLE 4

(±)-4-Amino-7-hydroxy-2-methyl-5,6,7,8-tetrahydrobenzo[b]thieno[2,3-b]pyridine-3-carboxylic acid, but-2-ynyl ester (E4, R$_4$=CH$_2$C≡CCH$_3$)

The title compound was prepared in 67% yield from the ketone D16 by a procedure similar to that outlined in Example 1, m.p. 216°–217° C.

NMR (CDCl$_3$) δ: 1.76–2.20 (6H, bm), 2.65–2.90 (4H, bm), 2.98–3.30 (3H, bm), 4.30 (1H, m), 4.88 (2H, q), 6.60 (2H, bs).

Found: C, 61.81; H, 5.47; N, 8.63% C$_{17}$H$_{18}$N$_2$O$_3$S requires C, 61.80; H, 5.49; N, 8.48%

EXAMPLE 5

(±)-4-Amino-7-hydroxy-2-methyl-5,6,7,8-tetrahydrobenzo[b ]thieno[2,3-b]pyridine-3-carboxylic acid, cyclobutylmethyl ester (E5, R$_4$=CH$_2$-c-C$_4$H$_7$)

The title compound was prepared in 64% yield from the ketone (D17) by a procedure similar to that outlined in Example 1, m.p. 191°–193° C.

NMR (CDCl$_3$) δ: 1.75–2.23 (9H, bm), 2.68 (3H, s), 2.70–2.88 (2H, bm), 3.00–3.35 (3H, bm), 4.30 (3H, m), 6.60 (2H, bm).

Found: C, 62.34; H, 6.30; N, 7.92% C$_{18}$H$_{22}$N$_2$O$_3$S requires C, 62.40; H, 6.40; N, 8.09%

EXAMPLE 6

(±)-4-Amino-7-hydroxy-2-methyl-5,6,7,8-tetrahydrobenzo[b]thieno[ 2,3-b]pyridine-3-carboxylic acid, cyclopropylmethyl ester (E6, R$_4$=CH$_2$-c-C$_3$H$_5$)

The title compound was prepared from the ketone D18 in 79% yield by a procedure similar to that of Example 1 as a pale yellow solid after recrystallisation from ethyl acetate, m.p. 204°–206° C.

NMR (CDCl$_3$) δ: 0.38 (2H, m), 0.65 (2H, m), 1.27 (1H, m), 1.85–2.25 (3H, m), 2.74 (3H, s), 2.81 (1H, m), 2.97–3.28 (3H, m), 4.16 (2H, d), 4.29 (1H, m), 6.57 (2H, bs),

Found: C, 61.32; H, 6.02; N, 8.48% C$_{17}$H$_{20}$N$_2$O$_3$S requires C, 61.43; H, 6.06; N, 8.43%

EXAMPLE 7

(±)-4-Amino-7-hydroxy-2-methyl-5,6,7,8-tetrahydrobenzo[b]thieno[2,3-b]pyridine-3-carboxylic acid, methyl ester (E7, R$_4$=CH$_3$)

The title compound was prepared from the ketone D19 in 55% yield by a procedure similar to that of Example 1 as a yellowish solid after recrystallisation from ethanol, m.p. 222°–225° C.

NMR (D$_6$-DMSO) δ: 1.78 (1H, m), 1.94 (1H, m), 2.52 (3H, s), 2.63 (1H, m), 2.92–3.17 (3H, bm), 3.87 (3H, s), 4.03 (1H, bm), 4.96 (1H, bs), 6.62 (2H, bs).

Found: C, 57.54; H, 5.30; N, 9.36% C$_{14}$H$_{16}$N$_2$O$_3$S requires C, 57.52; H, 5.52; N, 9.58%

EXAMPLE 8

(±)-4-Amino-7-hydroxy-2-methyl-5,6,7,8-tetrahydrobenzo[b]thieno[2,3-b]pyridine-3-carboxylic acid, prop-2-ynyl ester (E8, $R_4=CH_2C\equiv CH$)

The title compound was prepared in 68% yield from the ketone D20 by a procedure similar to that outlined in Example 1, m.p. 188°–190° C.

NMR ($D_6$-DMSO) δ: 1.68–2.00 (2H, bm), 2.45–2.70 (4H, bm), 2.90–3.18 (3H, bm), 3.65 (1H, m), 4.00 (1H, m), 4.98 (3H, m), 6.65 (2H, bs).

Found: C, 60.48; H, 5.20; N, 8.94% $C_{16}H_{16}N_2O_3S$ requires C, 60.74; H, 5.10; N, 8.85%

EXAMPLE 9

(±)-4-Amino-7-hydroxy-2-methyl-5,6,7,8-tetrahydrobenzo[b]thieno[2,3-b]pyridine-3-carboxylic acid, but-3-ynyl ester (E9, $R_4=CH_2CH_2C\equiv CH$)

The title compound was prepared in 58% yield from the ketone D21 by a procedure similar to that outlined in Example 1, m.p. 145°–150° C.

NMR (CDCl$_3$) δ: 1.90–2.05 (4H, bm), 2.65–2.90 (6H, bm), 3.00–3.30 (3H, bm), 4.30 (1H, m), 4.45 (2H, t), 6.64 (2H, bs).

Found: C, 61.37; H, 5.48; N, 8.34% $C_{17}H_{18}N_2O_3S$ requires C, 61.80; H, 5.49; N, 8.48%

EXAMPLE 10

(±)-4-Amino-7-hydroxy-2-methyl-5,6,7,8-tetrahydrobenzo[b]thieno[2,3-b]pyridine-3-carboxylic acid, but-3-enyl ester (E10, $R_4=CH_2CH_2CH=CH_2$)

The title compound was prepared in 87% yield from the ketone D22 by a procedure similar to that outlined in Example 1, m.p. 150°–152° C.

NMR (CDCl$_3$) δ: 2.00 (3H, m), 2.55 (2H, m), 2.70 (3H, s), 2.82 (1H, m), 3.00–3.30 (3H, bm), 4.28 (1H, m), 4.40 (2H, t), 5.08–5.27 (2H, bm), 5.78–5.97 (1H, bm), 6.60 (2H, bm).

Found: C, 61.11; H, 5.97; N, 8.35% $C_{17}H_{20}N_2O_3S$ requires C, 61.42; H, 6.06; N, 8.43%

EXAMPLE 11

(±)-4-Amino-7-hydroxy-2-methyl-5,6,7,8-tetrahydrobenzo[b]thieno[2,3-b]pyridine-3-carboxylic acid, propyl ester (E11, $R_4=CH_2CH_2CH_3$)

The title compound was prepared in 85% yield from the ketone D25 by a procedure similar to that outlined in Example 1, m.p. 182°–183° C.

NMR (CDCl$_3$) δ: 1.04 (3H, t), 1.70–2.23 (5H, bm), 2.72 (3H, s), 2.80 (1H, m), 2.95–3.27 (3H, bm), 4.27 (3H, m), 6.62 (2H, bs).

Found: C; 59.85, H; 6.32, N; 8.84% $C_{16}H_{20}N_2O_3S$ requires C; 59.98, H; 6.29, N; 8.74%

EXAMPLE 12

(±)-4-Amino-7-hydroxy-2-methyl-5,6,7,8-tetrahydrobenzo[b]thieno[2,3-b]pyridine-3-carboxylic acid, (2-methyl) propyl ester (E12, $R_4=CH_2CH(CH_3)_2$)

The title compound was prepared in 87% yield from the ketone D26 by a procedure similar to that outlined in Example 1, m.p. 188°–189° C.

NMR (CDCl$_3$) δ: 1.05 (6H, d), 1.84–2.20 (4H, bm), 2.74 (3H, s), 2.82 (1H, m), 2.97–3.28 (3H, bm), 4.13 (2H, d), 4.30 (1H, m), 6.65 (2H, bs).

EXAMPLE 13

(±)-4-Amino-7-hydroxy-2-phenyl-5,6,7,8-tetrahydrobenzo[b]thieno[2,3-b]pyridine-3-carboxylic acid, ethyl ester (E13)

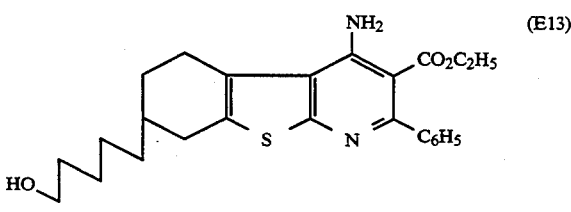

The title compound was prepared in 80% yield from the ketone D28 using a procedure similar to Example 1, m.p. 202°–203° C.

NMR (d$_6$-DMSO) δ: 0.67 (3H, t), 1.64–2.00 (2H, bm), 2.53–2.71 (1H, bm), 2.88–3.15 (3H, bm), 3.87 (2H, q), 3.96–4.09 (1H, bs), 4.93–5.03 (1H, bd), 6.41–6.52 (2H, bs), 7.37 (5H, s).

Found: C, 65.01; H, 5.57; 7.77%
$C_{20}H_{20}N_2O_3S$ requires C, 65.20; H, 5.47; N, 7.60%

EXAMPLE 14

(±)-4-Amino-7-hydroxy-2-methyl-5,6,7,8-tetrahydrobenzo[b]thieno[2,3-b]pyridine-3-carboxylic acid, pent-4-enyl ester (E14, $R_4=(CH_2)_3CH=CH_2$)

The title compound was prepared from the ketone D30 (0.80 g) by a procedure similar to that outlined in Example 1. Recrystallisation from ethanol afforded a white crystalline solid (0.42 g, 52%), m.p. 153°–155° C.

NMR (CDCl$_3$) δ: 1.82–2.27 (6H bm), 2.70 (3H, s), 2.81 (1H, m), 2.96–3.26 (3H, bm), 4.22–4.38 (1H, m, overlapping with 2H, t), 5.06 (2H, m), 5.84 (1H, m), 6.61 (2H, bs).

Found: C, 62.08; H, 6.35; N, 8.02% $C_{18}H_{22}N_2O_3S$ requires c, 62.40; H, 6.40; N, 8.09%

EXAMPLE 15

(±)-4-Amino-7-hydroxy-2-methyl-5,6,7,8-tetrahydrobenzo[b]thieno[2,3-b]pyridine-3-carboxylic acid, cyclohexyl ester (E15, $R_4=c\text{-}C_6H_{11}$)

The title compound was prepared in 73% yield from the ester D33 by a procedure similar to Example 1, m.p. 185°–6° C.

NMR (CDCl$_3$) δ: 1.20–2.20 (14H, bm), 2.71 (3H, s), 3.11 (2H, m), 4.29 (1H, bs), 5.07 (1H, m), 6.55 (2H, bs).

Found: C, 63.07; H, 6.60; N, 7.62% $C_{19}H_{24}N_2O_3S$ requires C, 63.31; H, 6.71; N, 7.77%

EXAMPLE 16

(±)-4-Amino-2-ethyl-7-hydroxy-5,6,7,8-tetrahydrobenzo[b]thieno[2,3-b]pyridine-3-carboxylic acid, ethyl ester (E16)

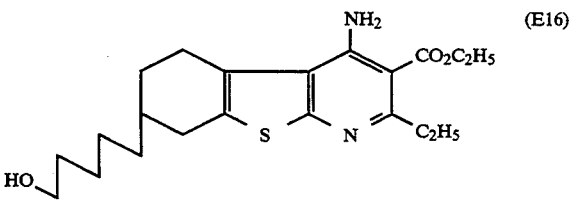

The title compound was prepared in 36% yield from the ketone D35 by a procedure similar to that outlined in Example 1, m.p. 175°-6° C.

NMR (CDCl$_3$) δ: 1.28 (3H, t), 1.42 (3H, t), 1.88–2.19 (3H, m), 2.72–2.88 (1H, bm), 2.93–3.28 (5H, m), 4.27 (1H, bm), 4.40 (2H, q), 6.37 (2H, bs).

Found: C, 59.79; H, 6.16; N, 8.66% C$_{16}$H$_{20}$N$_2$O$_3$S requires: C, 59.98; H, 6.29; N, 8.74%

EXAMPLE 17

(±)-4-Amino-7-hydroxy-2-methyl-5,6,7,8-tetrahydrobenzo[b]thieno[2,3-b]pyridine-3-carboxylic acid, cyclopropylethyl ester (E17, R$_4$=CH$_2$-c-CH$_2$-c-C$_3$H$_5$)

The title compound was prepared from the crude ketone D38 in 38% yield by the method of Example 1 after chromatography on silica with a gradient of 0–2% methanol/methylene chloride and recrystallization from methanol to give a white solid, m.p. 167.5°–169.5° C.

NMR(CDCL$_3$) δ: 0.13 (2H, m), 0.51 (2H, m), 0.82 (1H, m), 1.68 (2H, m), 1.90–2.20 (3H, bm), 2.72 (3H, s), 2.65–2.90 (1H, m overlapping with signal at 2.72), 2.95–3.30 (3H, m), 4.29 (1H, m), 4.40 (2H, t), 6.61 (2H, bs).

MS measured 346.1350, calculated for C$_{18}$H$_{22}$N$_2$O$_3$S 346.1351.

Found: C, 62.21; H, 6.30; N, 8.09% C$_{18}$H$_{22}$N$_2$O$_3$S requires: C, 62.40; H, 6.40; N, 8.09%

EXAMPLES 18 and 19

(±)-4-Dimethylamino-7-hydroxy-2-methyl-5,6,7,8-tetrahydrobenzo[b]thieno[2,3-b]pyridine-3-carboxylic acid, ethyl ester (E18)

(±)-4-Dimethylamino-7-methoxy-2-methyl-5,6,7,8-tetrahydrobenzo[b]thieno[2,3-b]pyridine-3-carboxylic acid, ethyl ester (E19)

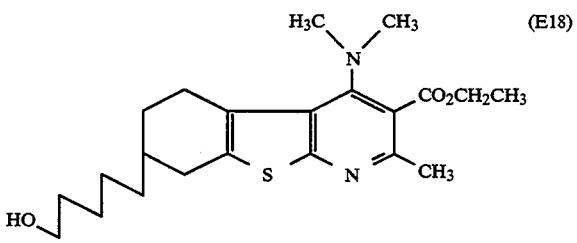

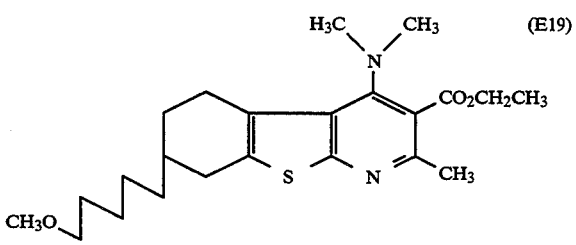

Sodium hydride (0.216 g, 7.2 mM, 80% dispersion in oil) was added with stirring under nitrogen to a solution of the alcohol E1 (1.0 g, 3.27 mM) in dry DMF (25 ml) at 0° C. The mixture was stirred for 0.5 h at this temperature and then methyl iodide (0.41 ml, 6.54 mM) added. After stirring for 4 days at room temperature the mixture was poured onto 20 water (200ml) and repeatedly extracted with dichloromethane. The combined organics were washed with water, dried over anhydrous sodium sulphate and evaporated to dryness. The residue, a brown gum, was chromatographed on silica gel with a gradient of 0–2.5% methanol/dichloromethane.

The trimethylated product E19 was obtained as a pale yellow gum, R$_f$0.77 on silica with 2.5% methanol/dichloromethane.

NMR (CDCl$_3$) δ: 1.43 (3H, t), 1.80–2.17 (2H, two overlapping m), 2.55 (3H, s), 2.75–3.30 (10H, overlapping m with s at 2.82), 3.46 (3H, s), 3.78 (1H, m), 4.43 (2H, q).

m/z=348(M+)

Later fractions afforded the dimethylated product E18 as a pale yellow gum (0.291 g, 27%), R$_f$0.4 on silica with 2.5% methanol/dichloromethane NMR (CDCl$_3$) δ: 1.42 (3H, t), 1.80–2.15 (3H, overlapping m), 2.55 (3H, s), 2.72–3.32 (10H overlapping m with s at 2.83), 4.30 (1H, bm), 4.42 (2H, q)

m/z=334(M+)

Pharmacological Data

1. Geller-Seifter Procedure

Potential anxiolytic properties have been evaluated using the Geller-Seifter procedure based on that originally described by Geller and Seifter, (1960) Psychopharmacologia, 1,482–492. This procedure has been shown to be selective for drugs with anxiolytic properties (Cook and Sepinwall, (1975) "Mechanism of Action of Benzodiazepines" ed. Costa, E. and Greengard, P., Raven Press, New York, pp. 1–28).

Rats are trained on a variable interval 30 sec schedule (VI30) to press a lever in order to obtain food reward. The 5 min sessions of the VI30 schedule alternate with 2–5 min of a schedule (FR5) in which every 5th lever press is followed by presentation of a food pellet paired with a 0.5 sec mild footshock. The total study lasts approximately 30 mins. Rats typically respond with high rates of lever pressing under the VI30 schedule and low response rates under the FR5 'conflict' session. Anxiolytic drugs increase the suppressed response rates of rats in 'conflict' session.

Drugs are administered intraperitoneally or orally to groups of 3–8 rats 30 min before testing.

The results are expressed as the percentage increase in square root of the total number of lever presses in the FR5 'conflict' session. Square root transformation is necessary to normalise the data for statistical analysis using parametric methods (ANOVA).

2. [$^{35}$S]-TBPS binding to rat cerebral cortex membranes in vitro

Pooled rat cerebral cortices are homogenised in 20 volumes of 0.32M sucrose and centrifuged at 1000 g for 20 minutes (4° C.). The supernatant is removed and recentrifuged at 50,000 g (4° C., 20 mins). The P$_2$ pellet is then suspended in 20 volumes of Tris citrate buffer (pH 7.1) and centrifuged at 50,000 g (4° C., 20 mins). This washing step is repeated three times and the pellet finally resuspended in 20 volumes of buffer and stored at −70° C. prior to use.

The tissue suspension (50 ml) is incubated (25° C., 120 mins) with [$^{35}$S]-TBPS (2 nM) in Tris citrate buffer (pH 7.1) containing 0.2M NaCl and 5×10$^{-6}$M GABA. Non-specific binding is measured in the presence of 10$^{-4}$M picrotoxin. Varying concentrations of test drugs (10$^{-7}$, 10$^{-6}$, 10$^{-5}$ and 10$^{-4}$M final concentration) are added in a volume of 50 ml. The total assay volume is 500 ml. Incubation is stopped by rapid filtration using a Skatron cell harvester and radioactivity measured by liquid scintillation spectrometry. IC$_{50}$'s are calculated as the concentration of test drug to inhibit 50% of specific binding.

3. MES Test

The maximal electroshock seizure (MES) test in rodents is one of the most widely used models of human grand mal epilepsy[1]. In this model, anticonvulsant agents elevate the threshold to electrically-induced seizures whilst proconvulsants lower the seizure threshold.

Method

Mice (male, Charles River, U.K. CD-1 strain, 25–30 g) are randomly assigned to groups of 10–20 and dosed orally or intraperitoneally at a dose volume of 10 ml/kg with various doses of compound (1–100 mg/kg) or vehicle. Mice are then subjected at 30 or 60 rain post dose to a variable voltage electroshock (0.1 sec., 50 Hz, sine wave form) via a buccal and a subcutaneous electrode. The mean voltage and standard error required to induce a tonic seizure in 50% ($CV_{50}$) of the mice in the group is determined by the 'up and down' method of Dixon and Mood (1948)[2]. Statistical comparisons between vehicle- and drug-treated groups are made using the method of Litchfield and Wilcoxon (1949)[3].

In control animals the $CV_{50}$ is usually 40–50 V. Hence the first animal in the control group is subjected to a voltage of 45 V. If a tonic seizure does not ensue, the voltage is increased for a subsequent mouse. If a tonic convulsion does occur, then the voltage is decreased, and so on until all the animals in the group have been tested.

The percentage increase or decrease in $CV_{50}$ for each group compared to the control is calculated.

Studies are carried out using a Heathkit shock generator with totally variable control of shock level from 0 to 200 V and voltage steps of 5 V are used.

Drugs are suspended in 1% methyl cellulose.

Reference

1. Swinyard, E. A. (1972). Electrically-induced convulsions. In: Experimental Models of Epilepsy ed. Purpura, D. P. et al., 433–458, Raven Press, New York.
Dixon, W. J. and Mood, A. M. (1948). J. Amer. Stat. Assn., 43, 109–126.
3. Litchfield, J. T. and Wilcoxon, F. (1949). J. Pharmacol. Exp. Ther. 96, 99–113.

Testing Results

1. Geller-Seifter procedure

Compounds of Examples 1, 4, 6, 7 and 10 showed a significant increase in responding in the 'conflict' session at 20 mg/kg p.o. and Examples 8 and 9 at 10 mg/kg p.o.

2. [$^{35}$S]-TBPS binding procedure

Compounds of Examples 1, 3, 4, 5, 6, 8 to 17 and 19 showed an $IC_{50}$ of less than 20 mM.

3. MES Test

Compound of Example 1 showed a significant increase in $CV_{50}$ at a dose of 100 mg/kg p.o.

We claim:

1. A compound of formula (I) or a pharmaceutically acceptable salt thereof:

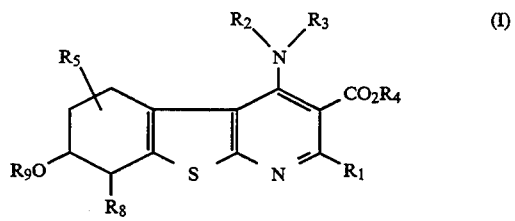

wherein:

$R_1$ is hydrogen, $C_{1-6}$ alkyl, phenyl or phenyl $C_{1-4}$ alkyl wherein the phenyl moiety is optionally substituted by one or more $C_{1-6}$ alkyl, $C_{1-6}$ alkoxy, $C_{1-6}$ alkylthio, hydroxy, $C_{2-7}$ alkanoyl, halo, trifluoromethyl, nitro, amino optionally substituted by one or two $C_{1-6}$ alkyl groups or by $C_{2-7}$ alkanoyl, cyano, carbamoyl or carboxy groups;

$R_2$ and $R_3$ are independently selected from hydrogen, $C_{1-6}$ alkyl, $C_{3-7}$ cycloalkyl, $C_{3-7}$ cycloalkyl-$C_{1-4}$ alkyl, $C_{3-6}$ alkenyl, $C_{1-7}$ alkanoyl, $C_{1-6}$ alkylsulphonyl, di-($C_{1-6}$ alkyl)amino $C_{1-6}$ alkyl, 3-oxobutyl, 3-hydroxybutyl, phenyl, phenyl $C_{1-4}$ alkyl, benzoyl, phenyl $C_{2-7}$ alkanoyl or benzenesulphonyl any of which phenyl moieties are optionally substituted by one or two halogen, $C_{1-6}$ alkyl, $C_{1-6}$ alkoxy, $CF_3$, amino or carboxy, or $R_2$ and $R_3$ together are $C_{2-6}$ polymethylene optionally interrupted by oxygen or $NR_6$ wherein $R_6$ is hydrogen or $C_{1-6}$ alkyl optionally substituted by hydroxy;

$R_5$ is hydrogen or $C_{1-6}$ alkyl and $R_8$ is hydrogen or $R_5$ and $R_8$ together form a $C_{1-6}$ alkylidene group at the 8-position;

$R_9$ is hydrogen or $C_{1-6}$ alkyl; and

—$CO_2R_4$ is a pharmaceutically acceptable ester group.

2. A compound according to claim 1 wherein $R_4$ is $C_{1-6}$ alkyl optionally substituted by up to three halo atoms, $C_{2-6}$ alkenyl, $C_{2-6}$ alkynyl, $C_{3-6}$ cycloalkyl or $C_{3-6}$ cycloalkyl-$C_{1-4}$ alkyl.

3. A compound according claim 1 wherein $R_1$ is hydrogen, $C_{1-3}$ alkyl, phenyl or benzyl.

4. A compound according to claim 1 wherein $R_2$ and $R_3$ are independently hydrogen or $C_{1-6}$ alkyl.

5. A compound according to claim 1 wherein $R_5$ and $R_8$ are both hydrogen.

6. A compound according to claim 1 wherein $R_9$ is hydrogen or methyl.

7. A compound of claim 1 selected frm the group consisting of:

(±)-4-Amino-7-hydroxy-2-methyl-5,6,7,8-tetrahydrobenzo[b]thieno [2,3-b]pyridine-3-carboxylic acid, ethyl ester;

(−)-4-Amino-7-hydroxy-2-methyl-5,6,7,8-tetrahydrobenzo[b]thieno [2,3-b]pyridine-3-carboxylic acid, ethyl ester;

(+)-4-Amino-7-hydroxy-2-methyl-5,6,7,8-tetrahydrobenzo[b]thieno [2,3-b]pyridine-3-carboxylic acid, ethyl ester;

(±)-4-Amino-7-hydroxy-2-methyl-5,6,7,8-tetrahydrobenzo[b]thieno [2,3-b]pyridine-3-carboxylic acid, but-2-ynyl ester;

(±)-4-Amino-7-hydroxy-2-methyl-5,6,7,8-tetrahydrobenzo[b]thieno [2,3-b]pyridine-3-carboxylic acid, cyclobutylmethyl ester;

(±)-4-Amino-7-hydroxy-2-methyl-5,6,7,8-tetrahydrobenzo[b]thieno [2,3-b]pyridine-3-carboxylic acid, cyclopropylmethyl ester;

(±)-4-Amino-7-hydroxy-2-methyl-5,6,7,8-tetrahydrobenzo[b]thieno [2,3-b]pyridine-3-carboxylic acid, methyl ester;

(±)-4-Amino-7-hydroxy-2-methyl-5,6,7,8-tetrahydrobenzo[b]thieno [2,3-b]pyridine-3-carboxylic acid, prop-2-ynyl ester;

(±)-4-Amino-7-hydroxy-2-methyl-5,6,7,8-tetrahydrobenzo[b]thieno [2,3-b]pyridine-3-carboxylic acid, but-3-ynyl ester;

(±)-4-Amino-7-hydroxy-2-methyl-5,6,7,8-tetrahydrobenzo[b]thieno [2,3-b]pyridine-3-carboxylic acid, but-3-enyl ester;

(±)-4-Amino-7-hydroxy-2-methyl-5,6,7,8-tetrahydrobenzo[b]thieno [2,3-b]pyridine-3-carboxylic acid, propyl ester;

(±)-4-Amino-7-hydroxy-2-methyl-5,6,7,8-tetrahydrobenzo[b]thieno [2,3-b]pyridine-3-carboxylic acid, (2-methyl) propyl ester;

(±)-4-Amino-7-hydroxy-2-phenyl-5,6,7,8-tetrahydrobenzo[b]thieno [2,3-b]pyridine-3-carboxylic acid, ethyl ester;

(±)-4-Amino-7-hydroxy-2-methyl-5,6,7,8-tetrahydrobenzo[b]thieno [2,3-b]pyridine-3-carboxylic acid, pent-4-enyl ester;

(±)-4-Amino-7-hydroxy-2-methyl-5,6,7,8-tetrahydrobenzo[b]thieno [2,3-b]pyridine-3-carboxylic acid, cyclohexyl ester;

(±)-4-Amino-2-ethyl-7-hydroxy-5,6,7,8-tetrahydrobenzo[b]thieno [2,3-b]pyridine-3-carboxylic acid, ethyl ester;

(±)-4-Amino-7-hydroxy-2-methyl-5,6,7,8-tetrahydrobenzo[b]thieno [2,3-b]pyridine-3-carboxylic acid, 2-cyclopropylethyl ester;

(±)-4-Dimethylamino-7-hydroxy-2-methyl-5,6,7,8-tetrahydro-benzo[b]thieno[2,3b]pyridine-3-carboxylic acid, ethyl ester;

(±)-4-Dimethylamino-7-methoxy-2-methyl-5,6,7,8-tetrahydro-benzo[b]thieno[2,3b]pyridine-3-carboxylic acid, ethyl ester;

or a pharmaceutically acceptable salt thereof.

8. A pharmaceutical composition which comprises a compound according to claim 1 and a pharmaceutically acceptable carrier.

9. A method for treatment of anxiety, convulsion and sleep disorders in mammals, which comprises administering to the sufferer an effective, non-toxic amount of a compound according to claim 1.

* * * * *